(12) United States Patent
Quinsac et al.

(10) Patent No.: US 11,490,875 B2
(45) Date of Patent: Nov. 8, 2022

(54) DEVICE FOR MEASURING BLOOD FLOW

(71) Applicant: AZOTH SYSTEMS, Ollioules (FR)

(72) Inventors: Céline Quinsac, Paris (FR); Axel Barbaud, Toulon (FR)

(73) Assignee: AZOTH SYSTEMS, Ollioules (FR)

( * ) Notice: Subject to any disclaimer, the term of this patent is extended or adjusted under 35 U.S.C. 154(b) by 249 days.

(21) Appl. No.: 16/473,165

(22) PCT Filed: Nov. 30, 2017

(86) PCT No.: PCT/FR2017/053334
§ 371 (c)(1),
(2) Date: Jun. 24, 2019

(87) PCT Pub. No.: WO2018/115617
PCT Pub. Date: Jun. 28, 2018

(65) Prior Publication Data
US 2020/0085406 A1 Mar. 19, 2020

(30) Foreign Application Priority Data

Dec. 23, 2016 (FR) ...................................... 16 63309

(51) Int. Cl.
*A61B 8/06* (2006.01)
*A61B 8/00* (2006.01)
*B63C 11/02* (2006.01)

(52) U.S. Cl.
CPC ............... *A61B 8/06* (2013.01); *A61B 8/4272* (2013.01); *A61B 8/4427* (2013.01);
(Continued)

(58) Field of Classification Search
CPC ... A61B 8/4272; A61B 8/4427; A61B 8/4455; A61B 8/4472; A61B 8/54; A61B 8/4477;
(Continued)

(56) References Cited

U.S. PATENT DOCUMENTS 5,396,891 A * 3/1995 Whitney .............. A61B 5/4504
600/449
6,962,566 B2 * 11/2005 Quistgaard ............. G01S 7/003
600/437
(Continued)

FOREIGN PATENT DOCUMENTS

CN 101889861 A 11/2010
JP 2014221161 A * 11/2014
WO WO 2015145011 A1 10/2015

OTHER PUBLICATIONS

A. Brubakk, et al., "Comparison of three different ultrasonic methods for quantification of intravascular gas bubbles," Undersea & Hyperbaric Medicine, vol. 28, No. 3, pp. 131-136, Fall 2001. (Year: 2001).*

(Continued)

*Primary Examiner* — Oommen Jacob
*Assistant Examiner* — Nyrobi Celestine
(74) *Attorney, Agent, or Firm* — von Briesen & Roper, s.c.

(57) ABSTRACT

The invention relates to a measurement device for the blood flow of an individual, for example for the detection of bubbles. The device comprises an acoustic emitter and a case with an emission surface capping the acoustic emitter. The emission surface is terminated at one end by a clavicular contact portion perpendicular to the emission surface and suited for coming to rest against a clavicle bone of the individual and is terminated at another end by a shoulder contact portion perpendicular to the emission surface and suited for coming to rest against a bone of the shoulder of the individual. A vertical distance between the middle of an active zone of the emission surface and the clavicular contact portion is less than 20 mm. A transverse distance (Continued)

between the middle of the active zone and the shoulder contact portion is included between 20 and 50 mm.

13 Claims, 5 Drawing Sheets

(52) U.S. Cl.
CPC .......... *A61B 8/4455* (2013.01); *A61B 8/4472* (2013.01); *A61B 8/4477* (2013.01); *A61B 8/54* (2013.01); *B63C 11/02* (2013.01); *B63C 2011/021* (2013.01)

(58) Field of Classification Search
CPC .................. A61B 8/445; A61B 8/06; A61B 2560/0406–0425; A61B 5/02028–02035; B63C 11/021; B63C 2011/021
See application file for complete search history.

(56) References Cited

U.S. PATENT DOCUMENTS

| | | | | |
|---|---|---|---|---|
| 7,549,964 | B2 * | 6/2009 | Kolasa | A61B 8/06 367/157 |
| 10,925,544 | B2 * | 2/2021 | Telfort | A61B 7/04 |
| 2006/0173331 | A1 * | 8/2006 | Booton | A61B 8/00 600/445 |
| 2009/0312643 | A1 * | 12/2009 | Ikegame | A61B 8/4455 600/459 |
| 2011/0313293 | A1 * | 12/2011 | Lindekugel | A61B 8/44 600/461 |
| 2012/0197118 | A1 * | 8/2012 | Lisiecki | A61B 8/4483 600/438 |
| 2013/0102901 | A1 * | 4/2013 | Ridley | A61B 17/3403 600/439 |
| 2013/0116538 | A1 * | 5/2013 | Herzog | A61B 5/0035 600/407 |
| 2014/0163374 | A1 * | 6/2014 | Ogasawara | A61B 8/4236 600/443 |
| 2014/0276077 | A1 * | 9/2014 | Morgan | A61B 8/4455 600/459 |
| 2014/0358000 | A1 * | 12/2014 | Gupta | A61B 8/13 600/441 |
| 2015/0305974 | A1 * | 10/2015 | Ehrenreich | A61H 23/0236 601/46 |
| 2016/0143627 | A1 * | 5/2016 | Vignon | A61B 8/466 600/437 |
| 2017/0332995 | A1 * | 11/2017 | Eibl | A61B 8/4281 |
| 2018/0206747 | A1 * | 7/2018 | Rinderknecht | A61B 5/6898 |

OTHER PUBLICATIONS

Z. Dujic, et al., "Acute effects of a single open sea air dive and post-dive posture on cardiac output and pulmonary gas exchange in recreational divers," British Journal of Sports Medicine, vol. 39, No. 5, pp. 1-7, Sep. 2004. (Year: 2004).*

A. Boussuges, et al., "Hemodynamic Changes Induced by Recreational Scuba Diving," Chest, vol. 129, No. 5, pp. 1337-1343, May 2006. (Year: 2006).*

A. L'Abbate, et al., "Post-dive ultrasound detection of gas in the liver of rats and scuba divers," European Journal of Applied Physiology, vol. 111, pp. 2213-2219, Feb. 2011. (Year: 2011).*

JP-2014221161-A (Year: 2014).*

International Search Report related to Application No. PCT/FR2017/053334; dated Jan. 30, 2018.

Edward O Belcher: "Quantification of Bubbles Formed in Animals and Man During Decompression", IEEE Transctions on Biomedical Engineering, IEEE Service Center, Piscataway, vol. BME-19, No. 6, Jun. 2, 1980, pp. 330-338, XPO11174588 NJ, USA.

Christian R. Gutvik et al: "Optimal Decompression of Divers [Applications of Control", IEEE Control Systems, IEEE, vol. 31, No. 1, Feb. 2, 2011, pp. 19-28, XPO11372726, USA.

Chinese First Office Action related to Application No. 201780086408.7; dated Jul. 6, 2021.

* cited by examiner

DEVICE FOR MEASURING BLOOD FLOW

CROSS-REFERENCE TO RELATED APPLICATION

This Application is, a 35 USC § 371 US National Stage filing of International Application No. PCT/FR2017/053334 filed on Nov. 30, 2017, and claims priority under the Paris Convention to French Patent Application No. 16 63309 filed on Dec. 23, 2016.

FIELD OF THE DISCLOSURE

The present disclosure relates to measurement devices for blood flow, in particular for decompression or other bubble detection operations.

With such a blood flow measurement, in particular, professional or amateur divers can check and monitor their exposure to pressure change effects, in particular for preventing decompression accidents.

The field of application of the present disclosure extends more generally to any type of monitoring of human exposure to a hyperbaric or hypobaric environment, in particular in the case of tunnel construction workers, during the use of hyperbaric caissons or saturation diving systems, or even in the aerospace domain; this list is obviously nonlimiting.

BACKGROUND OF THE DISCLOSURE

The present disclosure relates to devices for blood flow measurement and for detection, by acoustic waves, of bubbles in the blood of a portion of a person's cardiovascular system.

It is known to use a Doppler effect acoustic detection device, in particular an ultrasound probe, to perform bubble measurements in the blood flow of an individual.

An operator trained in performing Doppler measurements places the ultrasound probe on the chest of the diver and targets a chamber of interest, for example the right heart chambers which correspond to the venous return.

Usually the operator guides the positioning of the probe by means of the audio signal delivered by the probe, by trying to recognize the Doppler signal associated with the blood flow from the one or more targeted heart chambers and, if there are any, the Doppler signals characteristic of the presence of bubbles.

When the operator has identified, by ear, a signal that they associate with the correct positioning of the probe opposite the heart chambers, the operator usually does a rating of the signal heard.

The term "rating," is understood to mean counting or estimating the number of signals characteristic of bubbles heard among the heart flow signals.

The use of such a probe has several disadvantages.

The operator must be trained and experienced in recognition of the audio signals from the targeted chambers in order to be able to guide the positioning of the probe "by ear" in order to be able to recognize the characteristic signal of a good positioning of the probe. The operator can be mistaken if their ear is not sufficiently practiced and the probe can be incorrectly positioned and can detect the signal in a bad area.

In practice this prevents the use of such a measurement device and method by an operator untrained in the measurement of Doppler signals.

Further, even when the operator is trained in using such a positioning method, the method requires hearing an audio signal and this operation is not easy in a noisy environment.

The simple fact of needing to hear the signals of the decompression bubbles for positioning the probe can also cause a non-negligible risk. In fact, the passage of these bubbles can be particularly noisy and it has been observed that it is even able to cause unease or distress in the diver who hears them. The importance of this last disadvantage must not be underestimated because stress is a factor which favors the occurrence of a decompression accident.

There is therefore a need for a device with which a diver, or an operator not specifically trained to do it, can make blood flow measurements, in particular for the detection of decompression bubbles, simply, reliably, reproducibly and with little stress. There is also need for such a device which is low cost and robust such that in particular it can be used on each diving trip and therefore in an outside environment having sometimes difficult conditions (e.g. moisture, temperature, movement, etc.).

SUMMARY OF THE DISCLOSURE

For this purpose, the first object of the disclosure invention is a measurement device for the blood flow in a portion of the cardiovascular system of an individual, in particular for operations of bubble detection, the device comprising:

an acoustic emitter comprising at least one acoustic transducer suited for emitting an ultrasound beam and detecting a reflected ultrasonic signal, and a case in which the acoustic emitter is received.

The device is such that the case comprises an emission surface, substantially flat or convex, coming to cap the acoustic emitter to protect it from an outside environment and to assure the transmission of the ultrasound beam and the reflected ultrasonic signal, the emission surface extending substantially in a plane of vertical extension comprising a transverse direction and a perpendicular vertical direction so as to be able to come into contact with the skin of an individual along a longitudinal direction substantially perpendicular to the plane vertical extension, the emission surface being terminated at one end along the vertical direction by a clavicular contact portion substantially perpendicular to the emission surface and suited for coming to rest against a clavicle bone of the individual, the emission surface being terminated at one end along the transverse direction by a shoulder contact portion substantially perpendicular to the emission surface and suited for coming to rest against a bone of the shoulder of the individual, a vertical distance between the middle of the active zone of the emission surface and the clavicular contact portion being less than 20 mm, and a transverse distance between the middle of the active zone of the emission surface and the shoulder contact portion being included between 20 and 50 mm.

The aforementioned bubbles can be decompression bubbles or any other gas bubbles, in particular gas bubbles due to emboli.

In preferred embodiments of the disclosure, use could further be made of one and/or another of the following dispositions:

The transverse distance between the middle of the active zone and the shoulder contact portion is included between 30 and 40 mm;

The emission surface is terminated at two opposite transverse ends along the transverse direction by two shoulder contact portions substantially perpendicular to the emission surface and suited for coming to rest against a bone of the shoulder of the individual, and the middle of the active zone of the emission surface is located substantially equidistant from the shoulder contact portions along the transverse direction;

The case comprises an offset surface extending substantially in the plane of vertical extension and arranged recessed relative to the emission surface along the longitudinal direction so as to be suited for coming to press flat against the clavicle of the individual, in particular arranged with a recess distance along the longitudinal direction included between 5 and 15 mm;

The clavicular contact portion connects the emission surface to the offset surface, in particular the clavicular contact portion is connected to the offset surface by forming a quarter hollow so as to follow the curve of a clavicle of the individual;

The acoustic device further comprises at least one skin contact sensor suited for detecting a contact of the emission surface with the skin of the individual, in particular the device comprises two contact sensors arranged on either side of the acoustic emitter along the transverse direction;

One transducer of the acoustic emitter is inclined relative to the plane of vertical extension of the emission surface such that the direction of emission of the transducer is inclined towards the clavicular contact portion;

The acoustic emitter has a maximum dimension in the plane of vertical extension included between 30 and 40 mm, in particular the acoustic emitter comprises two acoustic transducers, more specifically the two acoustic transducers have an angle between their respective planes of extension included between 140 and 180°;

The case further receives acoustic emitter control and command electronics, where said electronics are laid out on at least one electronic card extending substantially along the plane of vertical extension, in particular the case further has a total dimension along the longitudinal direction of less than 50 mm;

The acoustic emitter control and command electronics comprise means for wireless communication with a base station such as a smart phone or computer.

BRIEF DESCRIPTION OF THE DRAWINGS

Other features and advantages will become apparent during the following description of several embodiments thereof, given as nonlimiting examples, with reference to the attached drawings.

In the drawings.

In the various figures, the same references designate identical or similar items.

DETAILED DESCRIPTION OF THE DISCLOSURE

Figure 1:
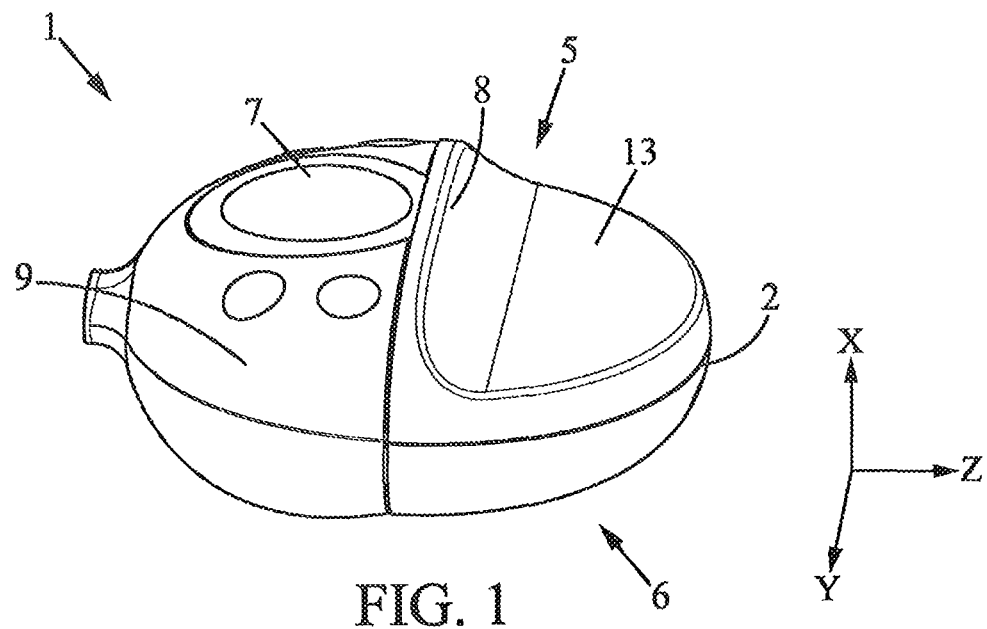
FIG. 1 is a schematic perspective view of a device according to an embodiment of the invention.

FIG. 1 shows a measurement device 1 for a blood flow according to an embodiment.

Figure 2:
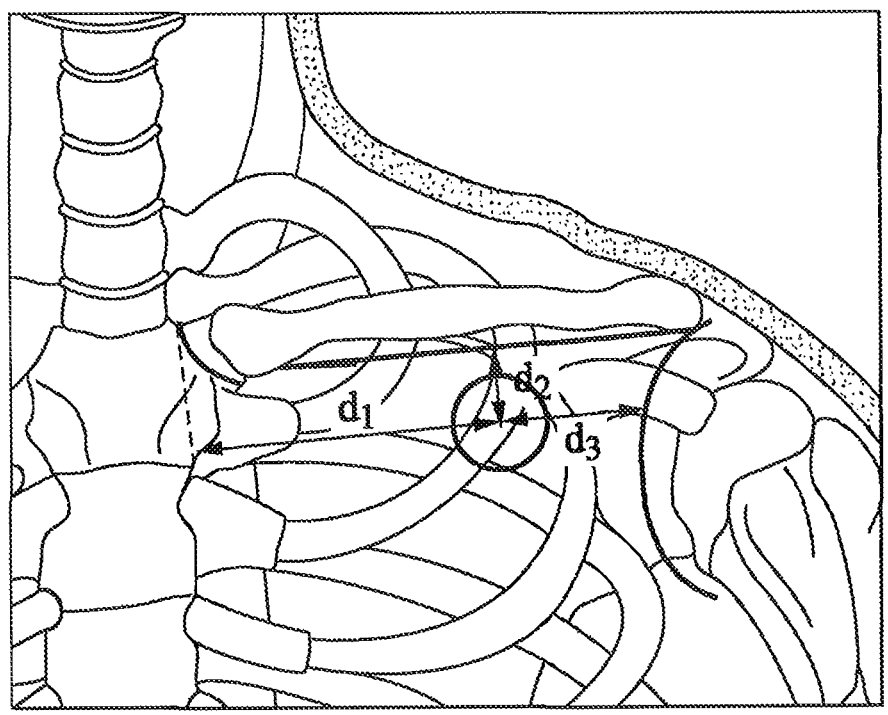
FIG. 2 is a schematic view of the skeleton of an individual showing in particular the positioning of the device.

One of the specifics of this device is being more specifically adapted to the measurement of blood flow in a precise portion of the cardiovascular system which is a subclavian vein such as shown in FIG. 2.

In fact the inventors observed that the subclavian veins, behind each clavicle of an individual, allow a more reproducible measurement than the measurement on the heart chambers and in particular make it possible to obtain a device providing a simplified positioning as is going to be described in the rest of the present description.

Figure 3:
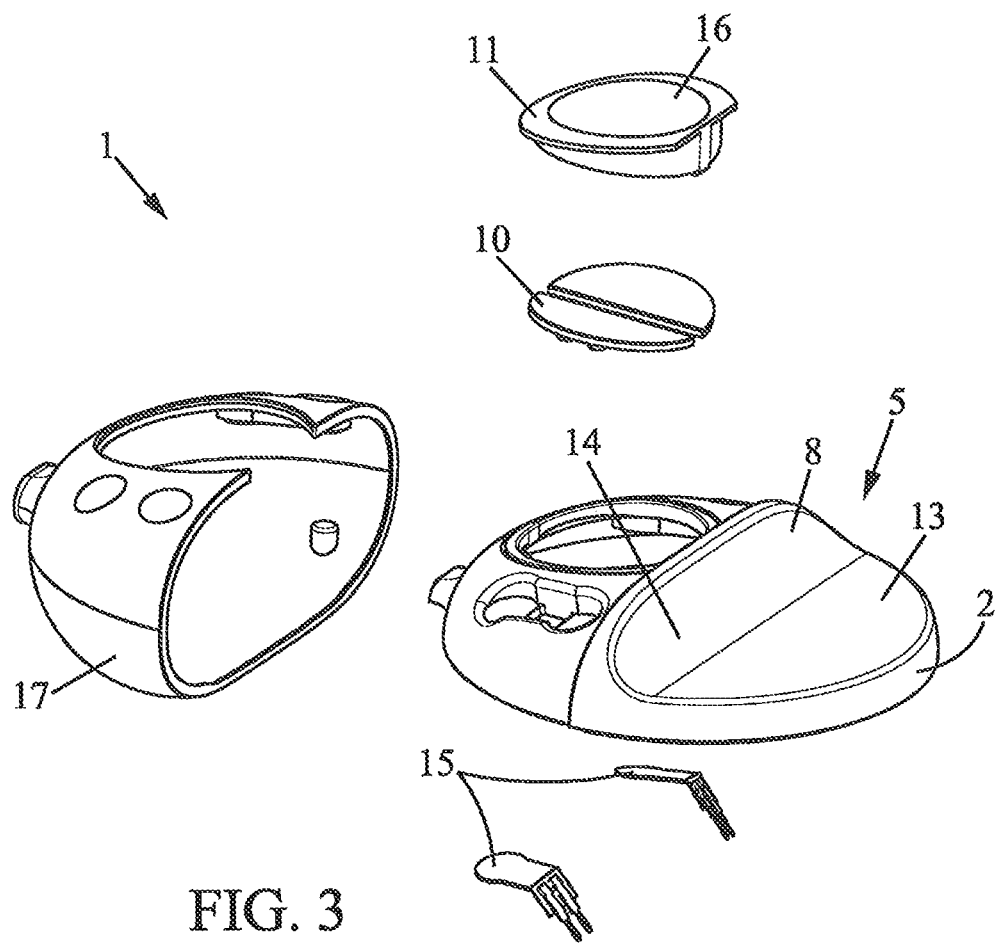
FIG. 3 is a section view of the device from FIG. 1.

The device 1 is in particular shown in FIG. 3 and comprises a case 2 receiving an acoustic emitter 3 and acoustic emitter control and command electronics 4 for the acoustic emitter.

Figure 4A:
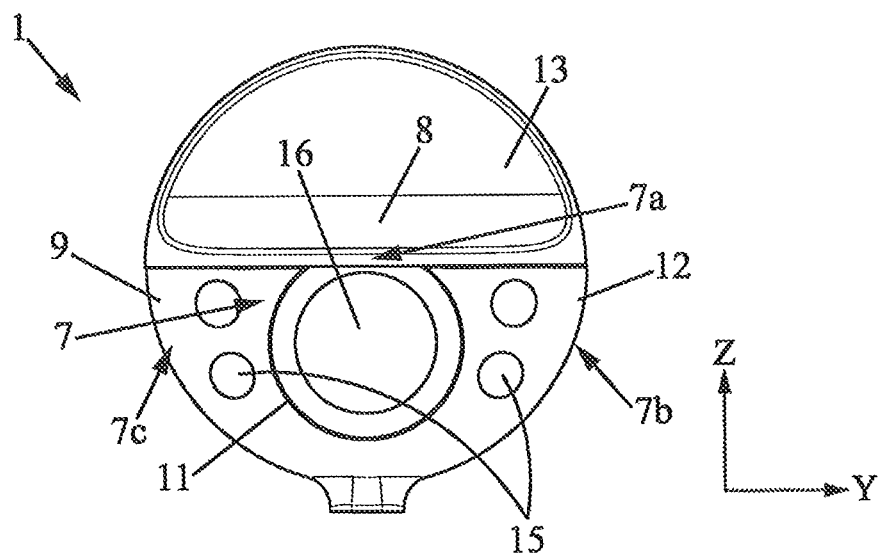
FIGS. 4A and 4B are respectively front and profile views of the device from FIG. 1.
Figure 4B:
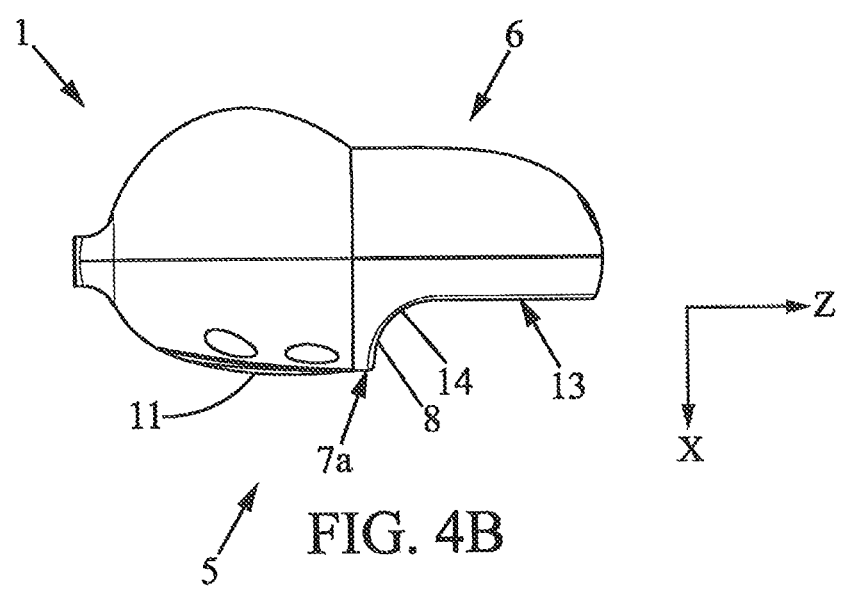

The case 2 is shown in particular in FIGS. 4A and 4B.

The case 2 extends principally along a plane of vertical extension Y, Z comprising a transverse direction Y and a vertical direction Z, which are perpendicular, and secondarily along a longitudinal direction X perpendicular to the plane of vertical extension.

In the example shown in the figures, the case 2 has the shape of a disk.

The case 2 thus comprises a first side 5 and a second side 6, opposite along the longitudinal direction X.

The first side 5 is suited for coming into contact with the skin of the thorax of the individual on whom the blood flow measurement is done.

The second side 6 is suited for the device 1 to be held in hand.

More specifically, the first side 5 comprises an emission surface 7 coming to cap the acoustic emitter 3.

A portion of the case can be surrounded by a contact cover 17, in particular a portion of the emission surface 7. The cover 17 is for example made of an elastomer for limiting sliding on the skin.

The emission surface 7 serves to protect the acoustic emitter 3 from the outside environment and to provide an acoustic impedance adaptation to the skin of the individual for the transmission of the ultrasound.

The emission surface can be formed of a single constituent or can comprise several sub-elements. The emission surface 7 can in particular comprise a convex lens 16, as shown in FIG. 3.

The lens 16 can be made of polyurethane, chosen for the low acoustic attenuation properties thereof.

The emission surface 7 is substantially flat or slightly convex and extends substantially along the vertical extension plane Y, Z. The emission surface 7 is terminated at the vertical and transverse ends by specific positioning portions of the probe which are now going to be described.

At a first end 7a along the vertical direction Z, the emission surface 7 ends with a clavicular contact portion 8 substantially perpendicular to the emission surface and suited for coming to rest against a clavicle bone of the individual along the vertical direction Z.

"Coming to rest against a clavicle bone of the individual along the vertical direction" is understood to mean that the individual can place the device against their skin below the clavicle, for example such that the emission surface is placed flat against the large pectoral muscle, and then move the device vertically until the clavicular contact portion 8 comes to rest against the clavicle of the individual from below along the vertical direction.

At a second end 7b along the transverse direction Y, the emission surface 7 is terminated by a shoulder contact portion 9 substantially perpendicular to the emission surface 7 and suited for coming to rest against a bone of the shoulder of the individual along the transverse direction Y.

"Coming to rest against a bone of the shoulder of the individual along the transverse direction" is understood to mean that the individual can place the device against their skin on the torso and near the shoulder, for example such that the emission surface is placed flat against the large pectoral muscle, and then move the device transversely until the shoulder contact portion 9 comes to rest against a bone of the shoulder of the individual from the side along the transverse direction.

Said bone of the shoulder of the individual can in particular be a portion of the scapula, for example a surface of the coracoid process.

In so far as possible, it is important to guarantee a close contact between the emission surface 7 and the skin of the individual. To do that, the device can further comprise at least one contact sensor 15. The contact sensor 15 can be capable of detecting a contact of the emission surface 7 with the skin of the individual.

The contact sensor 15 is, for example, a pressure sensor.

To confirm the proper positioning of the device, it can in particular comprise two contact sensors 15 arranged on each side of the acoustic emitter 3 along the transverse direction Y as shown in FIG. 4A.

Figure 5A:
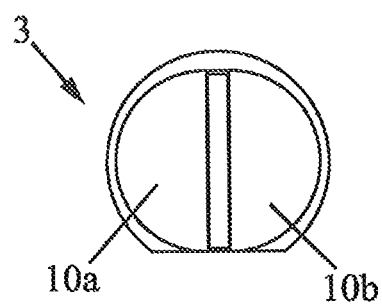
FIGS. 5A, 5B and 5C are respectively rear, left and top views of an acoustic emitter for the device, showing the lens and the acoustic transducers.
Figure 5B:
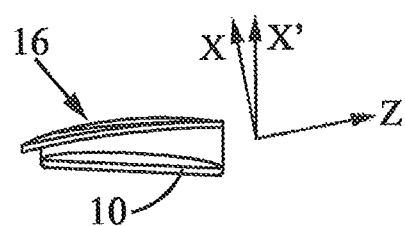
Figure 5C:
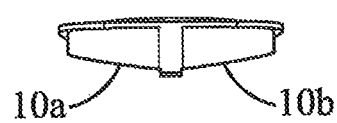

The acoustic emitter 3 comprises one or more acoustic transducers 10 which form an active area 11 and is shown in more detail in FIGS. 5A to 5C.

The acoustic transducers 10 are for example suited for operating in a range included between 2 MHz and 8 MHz, for example near 2 MHz.

The signal emitted and acquired by the acoustic transducers is for example defined and processed as is further known in the field of vascular ultrasound, for example vascular Doppler ultrasound.

In FIG. 5A for example, the acoustic emitter 3 comprises two acoustic transducers 10 each having a hemi-disk shape.

The acoustic transducers 10 of the acoustic emitter used during the measurement of the blood flow of the individual form an active area 11 on the emission surface 7. In the example from FIG. 5A, the active area 11 is thus in particular disk-shaped.

More precisely, the active zone 11 can comprise a slightly convex lens 16, as shown in FIG. 5B, which serves to reduce the presence of air bubbles between the acoustic transducers 10 and the skin of the individual.

The acoustic emitter 3, and in particular the active area 11 thereof can more precisely have a maximum dimension in the plane of vertical extension Y, Z included between 30 and 40 mm.

The clavicle contact portion 8 and the shoulder contact portion 9 are placed relative to the active zone 11 and in particular to the middle of the active zone in a precise way which is shown in FIG. 2.

"Middle of the active zone" is understood to mean a geometric barycenter of the active zone.

Thus, a vertical distance between the middle of the active zone 11 and the clavicular contact portion 8 is less than 20 mm, preferably less than 15 mm.

"Vertical distance" is understood to mean a distance measured along the vertical direction Z.

This vertical distance is shown by the reference d2 on FIG. 2.

Further, a transverse distance between the middle of the active zone 11 and the shoulder contact portion 9 is included between 20 and 50 mm, preferably between 30 and 40 mm.

"Transverse distance" is understood to mean a distance measured along the transverse direction Y.

This transverse distance is shown by the reference d3 on FIG. 2.

Another transverse distance is shown by the reference d1 on FIG. 2 and measures the distance along the transverse axis between the device 1 and the vertebral column of an individual.

In this way, the ultrasound signals emitted by the acoustic emitter 3 are suited for insonifying a portion of the subclavian vein.

More precisely, the acoustic emitter 3 can be arranged for further improving said insonification. Thus for example at least one transducer 10 from the acoustic emitter 3 can be inclined relative to the plane of vertical extension Y, Z of the emission surface 7. In particular, the direction of the emission X' of the transducer 10 which is substantially oriented along the longitudinal direction X of the device 1 can be inclined towards the clavicular contact portion 8.

For example, an angle between the direction of emission X' of the transducer 10 and the longitudinal direction X of the device 1 can be about 5°.

The acoustic transducers 10 can be non-coplanar and have an angle between them so as to control the acoustic beam width in the area of the subclavian vein and guarantee a better reproducibility of the measurements.

Thus in the example from FIG. 5C, two acoustic transducers 10a, 10b from the emitter 3 can have an angle between the respective planes of extension thereof less than 180°, in particular an angle included between 140 and 170°, for example an angle of about 160°.

The emitter 3 can in particular comprise two groups of transducers 10a, 10b. A first group 10a can comprise one or several transducers used in emission whereas the second group of transducers 10b can comprise one or several transducers used in reception. The functions of the two groups of transducers 10a and 10b can be exchanged over time.

In FIGS. 5A to 5C, the first and second groups of transducers 10a, 10b each comprise one single transducer and are symmetric.

In other embodiments, the two groups of transducers 10a, 10b can be asymmetric and different from each other.

Figure 6A:
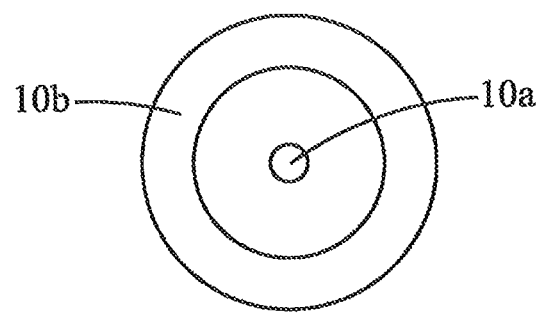
FIGS. 6A, 6B and 6C are rear views of an acoustic emitter for a the device according to three embodiments, showing in particular the position and shape of the acoustic transducers.

For example, in FIG. 6A, the first group 10a comprises a single circular and central emission transducer 10a. For its part, the second group of transducers 10b comprises a single receiving transducer 10b which is annular around the emission transducer 10a.

Figure 6B:
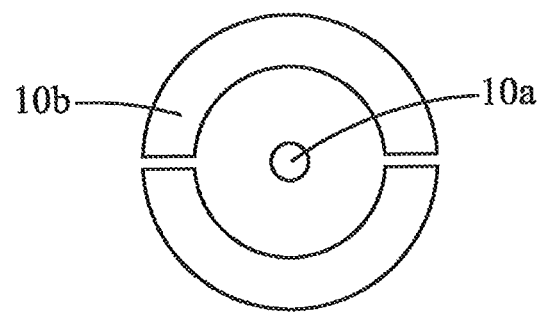
Figure 6C:
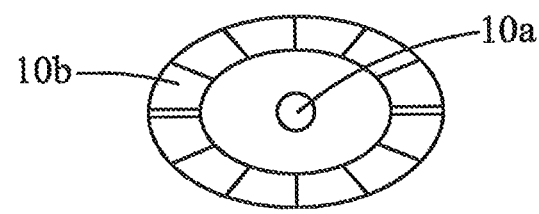

In FIGS. 10B and 10C, the second group of transducers comprises several transducers 10b (two in FIG. 6B and 12 in FIG. 6C) which are arranged around a central emission transducer 10a, with circular (in FIG. 6B) or oval (in FIG. 6C) shape.

Advantageously, as shown in FIG. 4A, the emission surface can be terminated at two opposite transverse ends 7b, 7c along the transverse direction by two shoulder contact portions 12, 9 substantially perpendicular to the emission surface 7 and suited for coming to rest against a bone of the shoulder of the individual.

Thus, in particular, the device 1 can be used to make a blood flow measurement both on the left and right subclavian vein.

In this embodiment, the middle of the active area 11 is in particular located substantially equidistant along the transverse direction Y from the shoulder contact portions 9, 12. The separation, along the transverse direction Y between the shoulder contact portions 9, 12, is thus substantially included between 40 and 100 mm, advantageously included between 60 and 80 mm.

To allow and even more precise positioning, the case 2 can comprise an offset surface 13.

The offset surface 13 can be arranged on the first side 5 of the device 1. The offset surface 13 is suited for coming to press flat against the clavicle of the individual.

In order to do that, the offset surface 13 can for example extend substantially in the plane of vertical extension Y, Z and be arranged recessed relative to the emission surface 7 along the longitudinal direction X so as to be adapted for coming to press flat against the clavicle of the individual.

The offset surface 13 can for example be arranged with a recess distance from the emission surface, along the longitudinal direction X, included between 5 and 15 mm.

As shown on FIGS. 4A and 4B, the offset surface 13 can be connected to the emission surface 7 via the clavicular contact portion 8.

In particular, the clavicular contact portion 7 can be connected to the offset surface 13 by a quarter hollow 14.

Such a quarter hollow 14 serves to better follow the curve of the clavicle of the individual and therefore improve the precision and reproducibility of the positioning of the device.

The device 1 is advantageously compact and suited for being easily grasped in just one hand by a diver wishing to make a measurement on their body.

To do that, the device 1 can in particular have a maximum dimension in the plane of vertical extension Y, Z less than 100 mm, advantageously less than 80 mm.

As shown in FIG. 3, the case 2 further receives acoustic emitter control and command electronics 4.

Advantageously the electronics 4 are arranged on a single electronic card 15 extending substantially along the plane of vertical extension Y, Z.

The case 2 can thus have a reduced dimension along the longitudinal direction X, for example a total dimension along the longitudinal direction X less than 50 mm.

The acoustic emitter control and command electronics 4 can in particular comprise means for wireless communication with a base station such as a smart phone or computer.

In this way, handling the device by an individual performing a measurement on their own body can be further simplified by avoiding the presence of cables.

Further, the acoustic emitter control and command electronics 4 can comprise a battery rechargeable by induction.

The presence of a connector is in that way avoided and the seal and resistance of the device are improved in hostile environments like the water's surface, for example.

The invention claimed is:

1. An acoustic device for measuring the blood flow in a portion of the cardiovascular system of an individual, in particular for operations of bubble detection, the device comprising:

an acoustic emitter comprising at least one acoustic transducer suited for emitting an ultrasound beam and detecting a reflected ultrasonic signal, and a case in which the acoustic emitter is received, wherein the case comprises an emission surface, flat or convex, coming to cap the acoustic emitter to protect it from an outside environment and to assure the transmission of the ultrasound beam and the reflected ultrasound signal, said emission surface having an active zone in correspondence with said acoustic emitter and said active zone having a middle, the emission surface extending in a plane of vertical extension comprising a transverse direction and a perpendicular vertical direction so as to be able to come into contact with the skin of the individual along a longitudinal direction perpendicular to the plane vertical extension, the emission surface being terminated at one end along the vertical direction by a clavicular contact portion perpendicular to the emission surface and suited for coming to laterally rest against a clavicle bone of the individual, the emission surface being terminated at one end along the transverse direction by a shoulder contact portion perpendicular to the emission surface and suited for coming to laterally rest against a bone of the shoulder of the individual when said clavicular contact portion is resting against said clavicle bone of the individual, a vertical distance between the middle of the active zone of the emission surface and the clavicular contact portion being less than 20 mm, and a transverse distance between the middle of the active zone of the emission surface and the shoulder contact portion being included between 20 and 50 mm, whereby the ultrasound beam insonifies a portion of a subclavian vein of the individual, wherein the case comprises an offset surface extending in the plane of vertical extension and arranged recessed relative to the emission surface along the longitudinal direction so as to be suited for coming to press flat against the clavicle of the individual while the emission surface is in contact with the chest of the individual, said offset surface being arranged with a recess distance along the longitudinal direction included between 5 and 15 mm, and wherein the clavicular contact portion connects the emission surface to the offset surface, the clavicular contact portion being connected to the offset surface by forming a quarter hollow so as to follow the curve of a clavicle of the individual.

2. The acoustic device according to claim 1, wherein the transverse distance between the middle of the active zone and the shoulder contact portion is included between 30 and 40 mm.

3. The acoustic device according to claim 1 wherein the emission surface is terminated at two opposite transverse ends along the transverse direction by two shoulder contact portions perpendicular to the emission surface and suited for coming to rest against a bone of the shoulder of the individual, and wherein the middle of the active zone of the emission surface is located equidistant from the shoulder contact portions along the transverse direction.

4. The acoustic device according to claim 1 further comprising at least one skin contact sensor suited for detecting a contact of the emission surface with the skin of the individual, in particular wherein the device comprises two contact sensors arranged on either side of the acoustic emitter along the transverse direction.

5. The acoustic device according to claim 1, wherein one transducer of the acoustic emitter is inclined relative to the plane of vertical extension of the emission surface such that the direction of emission of the transducer is inclined towards the clavicular contact portion.

6. The acoustic device according to claim 1, wherein the acoustic emitter has a maximum dimension in the plane of vertical extension included between 30 and 40 mm.

7. The acoustic device according to claim 1, wherein the case further receives acoustic emitter control and command electronics, where said electronics are laid out on at least one electronic card extending along the plane of vertical extension.

8. The acoustic device according to claim 7, wherein the acoustic emitter control and command electronics comprise a wireless communication device adapted to communicate wirelessly with a base station.

9. The acoustic device according to claim 8, wherein the base station is chosen in the group comprising a smart phone and a computer.

10. The acoustic device according to claim 6, wherein the acoustic emitter comprises two acoustic transducers.

11. The acoustic device according to claim 10, wherein the two acoustic transducers have an angle between their respective planes of extension included between 140 and 180°.

12. The acoustic device according to claim 7, wherein the case further has a total dimension along the longitudinal direction of less than 50 mm.

13. A method for measuring the blood flow in a portion of the cardiovascular system of an individual, in particular for operations of bubble detection, with a device comprising:
an acoustic emitter comprising at least one acoustic transducer suited for emitting an ultrasound beam and detecting a reflected ultrasonic signal, and
a case in which the acoustic emitter is received,
wherein the case comprises an emission surface, flat or convex, coming to cap the acoustic emitter to protect it from an outside environment and to assure the transmission of the ultrasound beam and the reflected ultrasound signal, said emission surface having an active zone in correspondence with said acoustic emitter and said active zone having a middle,
the emission surface extending in a plane of vertical extension comprising a transverse direction and a perpendicular vertical direction so as to be able to come into contact with the skin of the individual along a longitudinal direction perpendicular to the plane vertical extension,
the emission surface being terminated at one end along the vertical direction by a clavicular contact portion perpendicular to the emission surface and suited for coming to rest against a clavicle bone of the individual,
the emission surface being terminated at one end along the transverse direction by a shoulder contact portion perpendicular to the emission surface and suited for coming to rest against a bone of the shoulder of the individual when said clavicular contact portion is resting against said clavicle bone of the individual,
a vertical distance between the middle of the active zone of the emission surface and the clavicular contact portion being less than 20 mm, and
a transverse distance between the middle of the active zone of the emission surface and the shoulder contact portion being included between 20 and 50 mm,
the method comprising:
maintaining the case on the individual with said emission surface in contact with the chest of the individual, said clavicular contact portion resting laterally against said clavicle bone of the individual and said shoulder contact portion resting laterally against said bone of the shoulder of the individual,
emitting an ultrasound beam and detecting a reflected ultrasonic signal by said at least one acoustic transducer, said ultrasound beam insonifying a portion of a subclavian vein of the individual,
wherein the case comprises an offset surface extending in the plane of vertical extension and arranged recessed relative to the emission surface along the longitudinal direction so as to be suited for coming to press flat against the clavicle of the individual, said offset surface being arranged with a recess distance along the longitudinal direction included between 5 and 15 mm,
wherein the clavicular contact portion connects the emission surface to the offset surface, the clavicular contact portion being connected to the offset surface by forming a quarter hollow so as to follow the curve of a clavicle of the individual,
and wherein maintaining the case on the individual further includes having said offset surface pressing flat against the clavicle of the individual.

* * * * *